United States Patent
Nassutt et al.

(10) Patent No.: US 12,042,175 B2
(45) Date of Patent: Jul. 23, 2024

(54) BONE MATERIAL HARVESTING DEVICE

(71) Applicant: Stryker European Operations Limited, Carrigtwohill (IE)

(72) Inventors: Roman Nassutt, Kiel (DE); Torben Bröhan, Kiel (DE); Helge Giersch, Laboe (DE); Ronald Prager, Bovenau (DE)

(73) Assignee: Stryker European Operations Limited, Carrigtwohill (IE)

( * ) Notice: Subject to any disclaimer, the term of this patent is extended or adjusted under 35 U.S.C. 154(b) by 197 days.

(21) Appl. No.: 17/427,749

(22) PCT Filed: Feb. 7, 2020

(86) PCT No.: PCT/IB2020/000201
§ 371 (c)(1),
(2) Date: Aug. 2, 2021

(87) PCT Pub. No.: WO2020/165657
PCT Pub. Date: Aug. 20, 2020

(65) Prior Publication Data
US 2022/0226558 A1    Jul. 21, 2022

Related U.S. Application Data

(60) Provisional application No. 62/804,987, filed on Feb. 13, 2019.

(51) Int. Cl.
*A61B 17/34* (2006.01)
*A61M 1/00* (2006.01)
*A61M 25/00* (2006.01)

(52) U.S. Cl.
CPC ........... *A61B 17/3472* (2013.01); *A61M 1/60* (2021.05); *A61M 1/85* (2021.05); *A61M 1/76* (2021.05);
(Continued)

(58) Field of Classification Search
CPC .. A61M 2025/0039; A61M 1/84; A61M 1/60; A61M 1/85; A61M 1/76;
(Continued)

(56) References Cited

U.S. PATENT DOCUMENTS 1,696,018 A    12/1928   Schellberg
3,071,129 A *  1/1963    Wasserman .............. A61B 1/31
                                                       600/156
(Continued)

FOREIGN PATENT DOCUMENTS

EP        0675743 B1       9/1998
WO        9939724 A1       8/1999
WO        WO-0071016 A1 *  11/2000  ............. A61B 1/005

OTHER PUBLICATIONS

International Search Report for Application No. PCT/IB2020/000201, mailed Aug. 20, 2020, pp. 1-7.
(Continued)

*Primary Examiner* — Susan S Su
*Assistant Examiner* — Ted Yang
(74) *Attorney, Agent, or Firm* — Lerner David LLP (57) ABSTRACT

A bone harvesting device includes a main body having an internal cavity and a suction port adapted to be coupled to a suction source. The device further includes an outer tube (200) having an interior surface, an exterior surface, a proximal end and a distal end, the proximal end of the outer tube being coupleable to the main body, an inner tube having an interior surface, an exterior surface, a proximal end and a distal end, the inner tube being in fluid communication with the internal cavity and at least partially disposed within the outer tube such that a venting channel is defined between at least a portion of the inner tube and at least a portion of the outer tube.

7 Claims, 7 Drawing Sheets

(52) U.S. Cl.
CPC ............... *A61M 1/79* (2021.05); *A61M 1/86* (2021.05); *A61M 2025/0039* (2013.01); *A61M 2202/10* (2013.01)

(58) Field of Classification Search
CPC ...... A61M 1/79; A61M 1/86; A61M 2202/10; A61M 1/7411; A61M 1/742; A61B 17/32; A61B 17/3472; A61B 2010/0258; A61B 10/025; A61B 17/1635; A61B 2017/00969
See application file for complete search history.

(56) References Cited

U.S. PATENT DOCUMENTS

| | | | |
|---|---|---|---|
| 3,720,203 A | 3/1973 | Brown | |
| 4,300,550 A | 11/1981 | Gandi et al. | |
| 4,666,426 A | 5/1987 | Aigner | |
| 4,821,715 A | 4/1989 | Downing | |
| 4,857,045 A * | 8/1989 | Rydell | A61B 17/320758 606/159 |
| 5,024,615 A * | 6/1991 | Buchel | A61M 1/7411 433/95 |
| 5,269,785 A * | 12/1993 | Bonutti | A61B 10/025 606/167 |
| 5,368,017 A * | 11/1994 | Sorenson | A61M 16/0858 128/207.14 |
| 5,571,093 A | 11/1996 | Cruz et al. | |
| 6,022,354 A * | 2/2000 | Mercuri | A61B 17/1635 606/80 |
| 6,152,886 A * | 11/2000 | Phelan | A61M 1/7411 433/91 |
| 6,835,198 B2 * | 12/2004 | Bonutti | A61B 10/025 606/80 |
| 7,896,880 B2 * | 3/2011 | Bonutti | A61B 10/025 606/80 |
| 9,155,454 B2 * | 10/2015 | Sahney | A61B 17/42 |
| 10,405,886 B2 * | 9/2019 | Washburn, II | A61B 1/00108 |
| 10,750,931 B2 * | 8/2020 | Begg | A61B 1/015 |
| 10,772,652 B2 * | 9/2020 | Shener-Irmakoglu | A61B 1/018 |
| 10,772,654 B2 * | 9/2020 | Begg | A61B 17/42 |
| 11,602,588 B2 * | 3/2023 | Assell | C12M 45/00 |
| 2002/0058945 A1 | 5/2002 | Steiner | A61B 17/1635 606/80 |
| 2003/0009147 A1 * | 1/2003 | Bonutti | A61B 17/1635 604/500 |
| 2003/0078586 A1 * | 4/2003 | Shapira | A61B 17/1635 606/180 |
| 2003/0216690 A1 * | 11/2003 | Foley | A61M 1/7411 604/119 |
| 2004/0191897 A1 * | 9/2004 | Muschler | A61B 17/32002 435/325 |
| 2004/0243157 A1 * | 12/2004 | Connor | A61M 3/0283 606/159 |
| 2007/0016100 A1 | 1/2007 | Miller | |
| 2007/0055282 A1 * | 3/2007 | Muschler | A61B 10/025 606/92 |
| 2008/0243029 A1 * | 10/2008 | Howard | A61M 1/79 600/565 |
| 2009/0228030 A1 * | 9/2009 | Shadeck | A61M 1/742 606/167 |
| 2009/0287190 A1 * | 11/2009 | Shippert | A61M 1/604 604/542 |
| 2009/0306669 A1 | 12/2009 | Takahashi | |
| 2010/0168692 A1 * | 7/2010 | Collins | A61M 1/916 604/319 |
| 2012/0289941 A1 * | 11/2012 | Salehi | A61C 17/135 604/540 |
| 2013/0053725 A1 | 2/2013 | Beck et al. | |
| 2013/0245613 A1 * | 9/2013 | Salehi | A61M 1/7411 604/540 |
| 2015/0359950 A1 * | 12/2015 | Salehi | A61C 17/08 604/540 |
| 2016/0038660 A1 * | 2/2016 | Loebl | A61M 1/85 604/35 |
| 2016/0278790 A1 | 9/2016 | Nassutt et al. | |
| 2018/0078243 A1 * | 3/2018 | Rocha-Singh | A61B 17/22004 |
| 2018/0214217 A1 * | 8/2018 | Rodriguez | A61M 25/0905 |
| 2018/0250029 A1 * | 9/2018 | Begg | A61B 17/42 |
| 2018/0344327 A1 * | 12/2018 | Jeng | A61B 17/1635 |
| 2019/0374688 A1 * | 12/2019 | Palushi | A61M 1/86 |
| 2020/0100800 A1 * | 4/2020 | Seykora | A61B 17/1635 |
| 2020/0179579 A1 * | 6/2020 | Arnone | A61M 1/774 |

OTHER PUBLICATIONS

Marchand, Lucas S., et al, "Is This Autograft Worth It? The Blood Loss and Transfusion Rates Associated With Reamer Irrigator Aspirator Bone Graft Harvest", Apr. 2017, vol. 31, No. 4, pp. 205-209.

Partial International Search Report including Provisional Opinion for Application No. PCT/IB2020/000201, mailed Jun. 29, 2020, pp. 1-9.

Wenisch, S. et al. titled "Human reaming debris: a source of multipotent stem cells", Bone 36, 2005, pp. 74-83.

* cited by examiner

BONE MATERIAL HARVESTING DEVICE

CROSS-REFERENCE TO RELATED APPLICATIONS

The present application is a national phase entry under 35 U.S.C. § 371 of International Application No. PCT/IB2020/000201 filed Feb. 7, 2020, which claims the benefit of the filing date of U.S. Provisional Patent Application No. 62/804,987 filed Feb. 13, 2019, the disclosures of which are hereby incorporated herein by reference.

BACKGROUND OF THE INVENTION

The present invention relates to devices and methods for harvesting and processing bone and/or cellular material for use in various medical treatments.

Pseudarthrosis, also referred to as non-union of bone, is a common complication of fracture treatment. Non-union occurs when a particular patient's fracture site fails to heal within a specified period of time, and thus requires an intervention (e.g., surgical) in order to achieve proper union and mobility. In some cases, non-unions may be treated by bone grafting (e.g., allograft, autograft, or xenograft), through internal or external fixation, or a combination thereof. Bone grafting offers an opportunity to stimulate the fracture site so that bony formation occurs at the site to properly unionize the fracture.

Stem cells (e.g., Mesenchymal stem cells (MSCs), hematopoietic stem cells (HSCs), or other stem cells) are known to be useful with certain graft materials, or by themselves, to facilitate bone growth and formation when used appropriately. For example, adult MSCs are capable of differentiating into a variety of different cell types including osteoblasts (bone cells), chondrocytes (cartilage cells), and adipocytes (fat cells). As such, when incorporated with certain allograft material, stem cells can assist with the proper formation of bone and union of bone parts at a fracture site. Stem cells of the type discussed above must first be extracted from a patient and processed before use. As an example, extracted bone marrow of a patient can provide the necessary stem cells.

Bone marrow is typically extracted in a multi-staged procedure. In a first stage of the procedure, bone marrow is aspirated from a patient and then sent to a laboratory for processing. It is only then, in a second stage of the procedure, that the previously harvested bone marrow is processed for the patient's particular application. Bone marrow from the iliac crest is widely considered the "gold standard" for its superior biologic quality. The drawback of harvesting bone marrow from the iliac crest, however, is that the iliac crest naturally produces a limited quantity of marrow. For surgical interventions requiring a higher volume of bone marrow, such as trauma and orthopedic applications, bone marrow is often harvested from the medullary canal of a long bone (e.g., the femur or tibia), which naturally produces a higher volume of bone marrow than the iliac crest. Bone marrow harvested from the medullary canal has proven to be an effective alternative to bone marrow harvested from the iliac crest and is capable of providing significant regenerative potential.

In order to harvest the desired volume of marrow from the medullary canal, a surgeon must access and aspirate bone marrow located deep within the bone canal. This procedure is often performed using a harvesting system that is typically equipped with a reamer, an irrigation system, a suction source (OR suction) and a filter. Although these systems are generally sufficient in harvesting the desired bone material, they are aggressive and carry significant clinical risks such as severe blood loss that often necessitates blood transfusion treatments. In fact, while the medical community appreciates the regenerative potential of bone marrow harvested from the medullary canal of long bone, some medical professionals have begun to question whether harvesting the autograft materials is worth the significant clinical risks.

Known harvesting devices are also susceptible to clogging, which results in decreased aspiration function, especially while positioned deep within the medullary canal. Moreover, the harvested material is often diluted and/or contaminated by the water or other solution introduced by the irrigation system. Such dilution or contamination complicates the processing stage of the procedure and necessitates additional filtering or refining of the harvest. Therefore, new and improved bone harvesting devices and methods that address these shortcomings are desired.

BRIEF SUMMARY OF THE INVENTION

In accordance with a first aspect of the present invention, a device for harvesting bone and/or cellular material (e.g., cancellous bone, bone chips, bone marrow, and stem cells) for use in various medical applications is provided. Among other advantages, the device includes a dual tubed aspiration assembly that reduces clogging and improves aspiration efficiency. In part, due to the improved aspiration efficiency, the device is capable of performing clog-free transportation of even highly viscous material without the irrigation of fluids. As a result, the need for subsequent filtering and excessive processing is eliminated. Furthermore, the improved aspiration function reduces the surgeon's impulse to aggressively drill into the bone and, in turn, reduces the likelihood of severe blood loss and the clinical complications associated with sever blood loss.

One embodiment of the bone harvesting device includes a main body having an internal cavity and a suction port adapted to be coupled to a suction source, an outer tube having an inner surface, an outer surface, a proximal end and a distal end, the proximal end of the outer tube being coupleable to the main body, an inner tube having an inner surface, an outer surface, a proximal end and a distal end, the inner tube being coupleable to the main body and at least partially disposed within the outer tube such that the inner tube is in fluid communication with the internal cavity, and a storage container coupleable to the main body such that the storage container is in fluid communication with the internal cavity for receiving bone and/or cellular material extracted from the patient.

In some embodiments, the storage container includes an outer sidewall extending from a base end to a top end, and an inner sidewall at least partially disposed within the outer sidewall and being concave with respect to the top end, the inner sidewall defining a collection space for receiving the extracted bone and/or cellular material. At least a portion of the inner sidewall is spaced a distance from the outer sidewall.

In another embodiment, the bone harvesting device may include a body having an internal cavity and a suction port adapted to be coupled to a suction source, an outer tube having an inner surface, an outer surface, a proximal end and a distal end, the proximal end of the outer tube being coupleable to the body, and an inner tube having an inner surface, an outer surface, a proximal end and a distal end. The inner tube may be in fluid communication with the internal cavity and at least partially disposed within the outer tube such that a venting channel is defined between at least a portion of the inner tube and at least a portion of the outer tube.

A method of collecting bone and/or cellular material during a bone harvesting procedure is also provided herein. The method includes the steps of (a) operating a reaming, milling, or drilling tool so that the tool reams, mills, or drills into a canal of a bone to generate bone and/or cellular material, (b) inserting a bone harvesting tool into the bone canal, the bone harvesting tool comprising an inner tube at least partially disposed within an outer tube such that a ventilation channel is formed between the inner and outer tubes, (c) generating negative pressure within an internal cavity of a bone harvesting tool, the negative pressure causing the bone and/or cellular material to flow from the patient through the inner tube and into the internal cavity of the bone harvesting tool, and collecting the bone and/or cellular material in a storage container fluidly connected to the internal cavity of the bone harvesting tool.

DETAILED DESCRIPTION

As used herein, "axial" means along or parallel to the longitudinal axis of the bone harvesting device and "radial" means in the perpendicular direction thereto. "Interior" or "inner" means radially inward, either toward or facing the longitudinal axis, and "exterior" or "outer" means radially outward, or away from the longitudinal axis. The terms "proximal" and "distal" refer, respectively, to the end of the device nearest the surgeon or other user operating the device, and the opposite end of the device furthest from the user operating the device.

Figure 1:
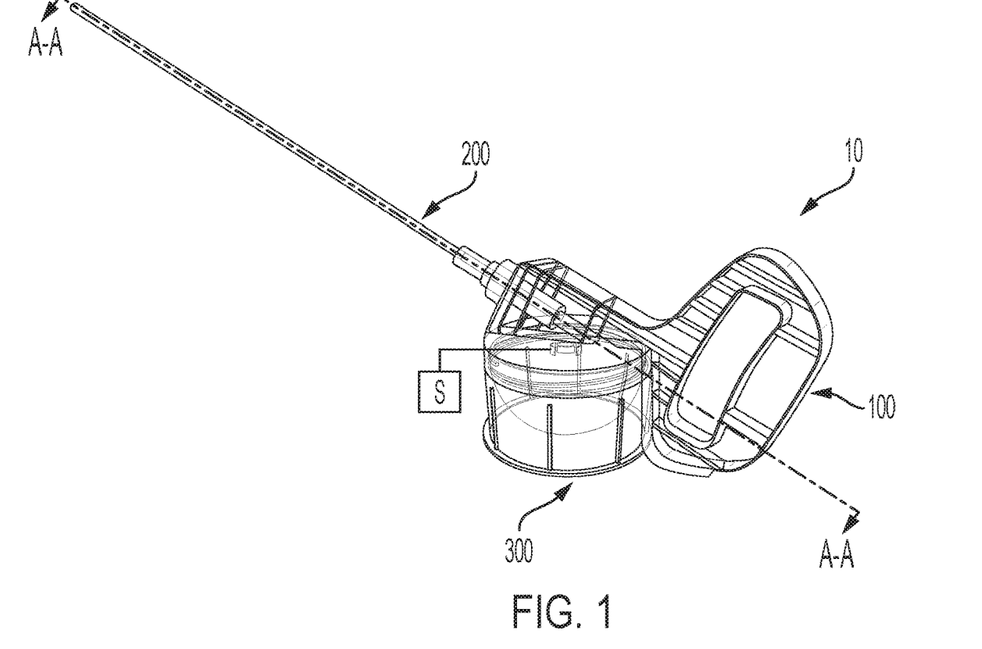
FIG. 1 is a perspective view of a bone harvesting device according to an embodiment of the invention.
Figure 2:
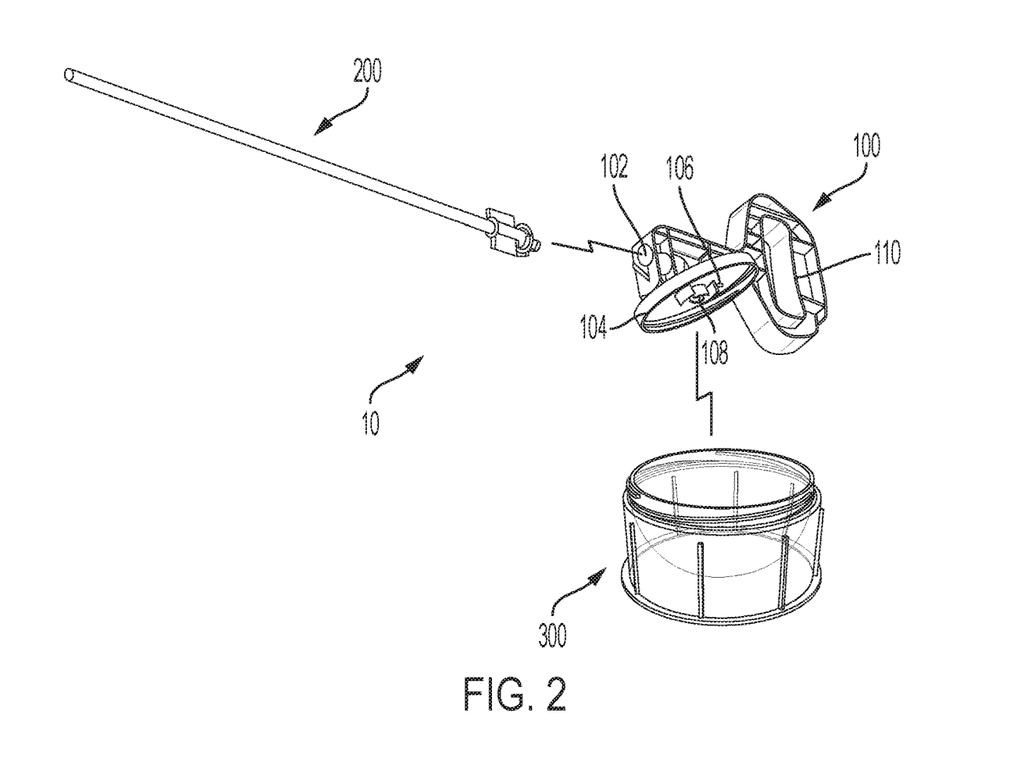
FIG. 2 is an exploded view of the bone harvesting device of FIG. 1.

Bone harvesting device 10, as shown in FIGS. 1 and 2, includes a body 100, an aspiration assembly 200 for aspirating bone and/or cellular material from a patient, and a collection storage container 300 for collecting the aspirated material. The phrase bone and/or cellular material refers to material that is extractable from bone, which may optionally then be processed and/or separated to produce another material. For instance, bone and/or cellular material may include cancellous bone, cortical bone (in the form of chips or morselized bone), bone marrow, or stem cells produced from any of the foregoing materials. Such materials are frequently found, for example, in the iliac crest, or the medullary canal of a long bone, as well as the bone surrounding the medullary canal. Bone harvesting device 10 may be formed entirely, or in part, from a transparent medical grade glass or plastic, thereby permitting an operator using the device to observe the collection of bone and/or cellular material during a harvesting procedure.

Main body 100 includes a first connector, for example, a threaded bore 102, for removably securing aspiration assembly 200 to the body, and a second connector, for example, a threaded, lid-shaped platform 104 for removably securing storage container 300 to the body. It will be appreciated, however, that the first and second connectors need not include threads. Instead, aspiration assembly 200 and storage container 300 may alternatively be coupled to the main body 100 via an interference or snap-fit connection, or any other connector known in the art. Main body 100 also defines a suction port 106, for example, in lid-shaped platform 104 that is configured to be coupled to a suction source S such as a standard operating room suction source (OR suction). Suction port 106 may include a filter to prevent bone and/or cellular material from being drawn from storage container 300 into a suction tube connected suction source S.

With specific reference to FIG. 2, platform 104 has an aperture 108 that allows harvested bone and/or cellular material to flow from aspiration assembly 200 and into storage container 300 during a harvesting procedure. As shown, main body 100 may also include an ergonomically shaped handle 110 to aid a surgeon in positioning the bone harvesting device during operation.

Figure 3:
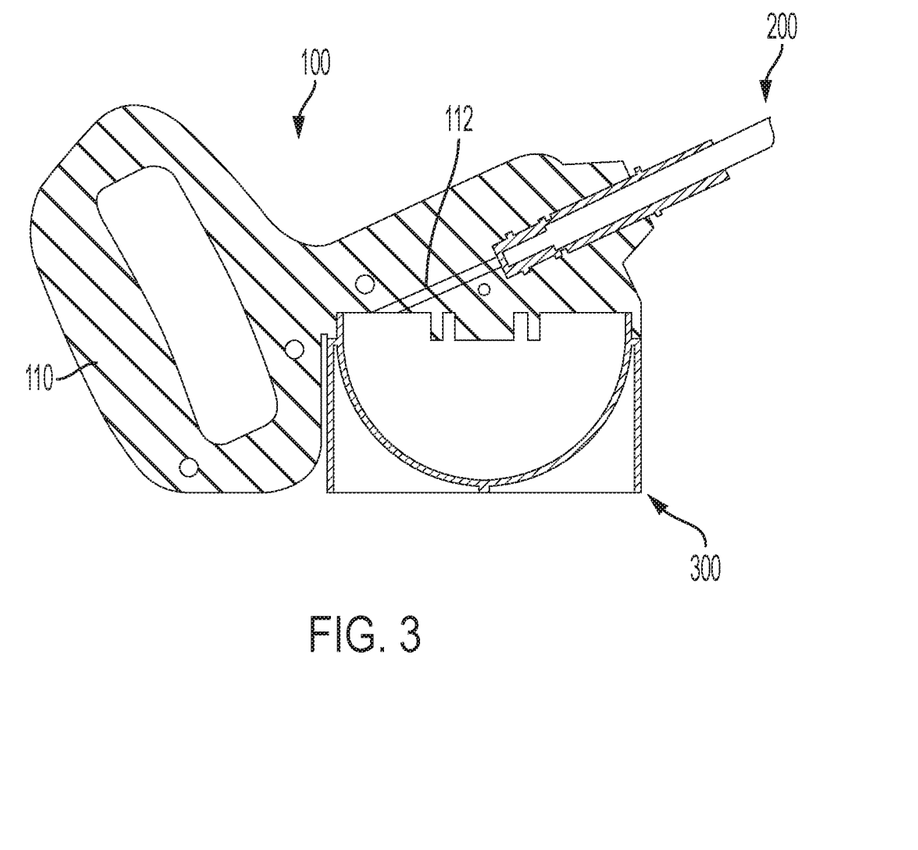
FIG. 3 is a partial cross-section of the bone harvesting device of FIG. 1 taken along line A-A.

Referring to FIG. 3, main body 100 defines an internal cavity 112 that is in fluid communication with aspiration assembly 200 and suction source S. Thus, when OR suction is applied, a negative pressure is produced within internal cavity 1120. This negative pressure draws bone and/or cellular material through aspiration assembly 200, into the internal cavity, through the aperture 108 and into storage container 300.

Aspiration assembly 200, as shown in FIGS. 4A-4D, includes a generally hollow adapter housing 202, an outer tube 204 and an inner tube 206. Outer tube 204 and inner tube 206 are formed of a resilient and flexible material that allows the tubes to bend, with respect to the main body 100 and with respect to one another, as the aspiration assembly navigates through the medullary canal of a long bone. Aspiration assembly 200 defines a length between a proximal end 208 and a distal end 210 of the assembly. Bone harvesting device 10 may include a single aspiration assembly 200 measuring approximately 500 mm in length, or a plurality of interchangeable aspiration assemblies having various lengths for harvesting bone of different length.

Figure 4A:
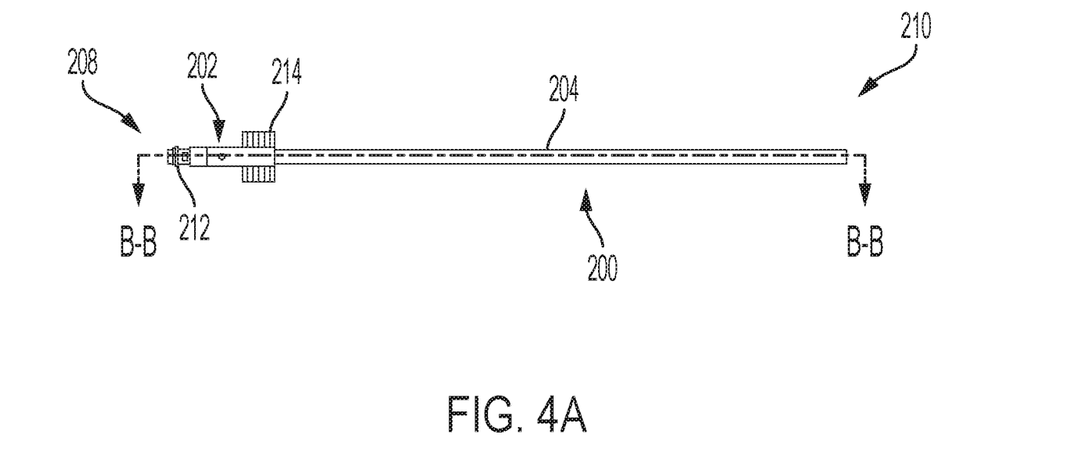
FIG. 4A is a side view of an aspiration assembly of the bone harvesting device of FIG. 1.

The proximal end 208 of aspiration assembly 200 includes threads 212 for threading adapter 202 within the bore 102 of main body 100. Adapter 202 need not include threads, however, as aspiration assembly 200 may instead be removably coupled to main body 100 by an interference or snap fit connection, or any other connector known in the art. Adaptor 202 may also include a flange 214, or similar protrusion having an ergonomic grip to aid a user in coupling and/or decoupling the aspiration assembly 200 to the main body 100.

Figure 4B:
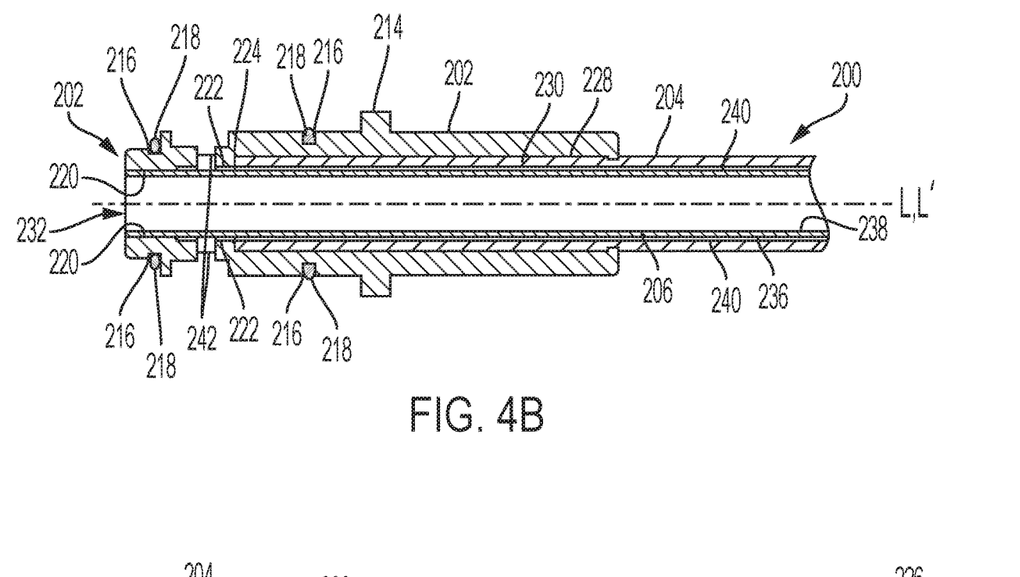
FIG. 4B is an enlarged, partial cross-section view of the proximal end of the aspiration assembly of FIG. 4A taken along line B-B.

With specific reference to FIG. 4B, adaptor 202 has one or more annular grooves 216 within its exterior surface. A gasket 218, such as an O-ring, is provided within each groove 216 to seal the space between the adaptor 202 and the bore 102 of the main body at each location. Adapter 202 also includes first and second inwardly projecting ledges 220, 222. The first ledge 220 is provided adjacent the proximal end of adapter 202, while the second ledge 222 is positioned between the first ledge and the flange 214. First ledge 220 protrudes further into the interior space of the adapter 202 than the second ledge 222.

Figure 4C:
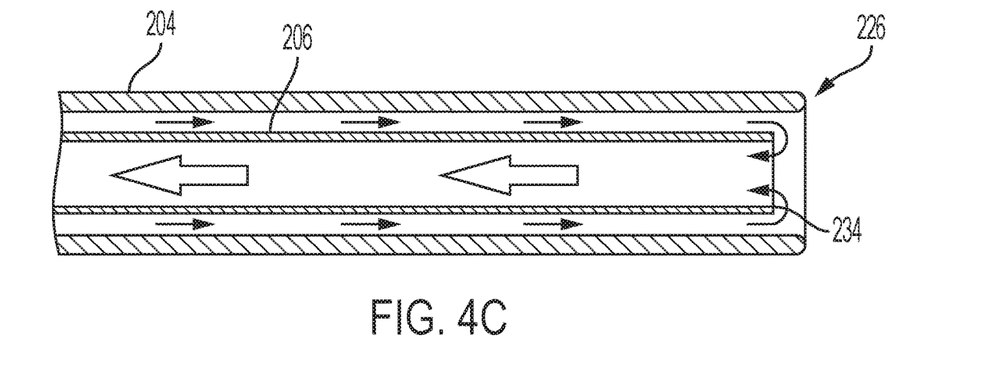
FIG. 4C is an enlarged, partial cross-section view of the distal end of the aspiration assembly of FIG. 4 taken along line B-B.

Outer tube 204 extends along a longitudinal axis L from a proximal end 224 to a distal end 226 and includes an exterior surface 228 and an interior surface 230. The exterior surface 228 of outer tube 204 engages the interior surface of adapter 202, while the proximal end 224 of the outer tube is bonded, welded, glued or otherwise sealed to a distal facing surface of the second ledge 222. The distal end 226 of outer tube 204 is preferably rounded, as shown in FIG. 4C, to reduce trauma as aspiration assembly 200 is operated within the medullary canal of bone.

Inner tube 206, which is positioned at least partially within outer tube 204, extends along a longitudinal axis L' from a proximal end 232 to a distal end 234 and includes an exterior surface 236 and an interior surface 238. Inner tube 206 is bonded, welded, glued or otherwise sealed to an inwardly facing surface of the first ledge 220, thereby forming a venting channel 240 between the inner and outer tubes.

Figure 4D:
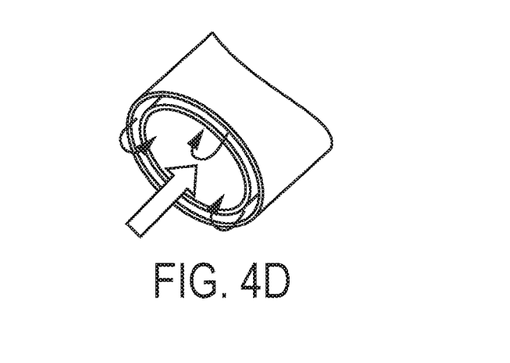
FIG. 4D is a partial, front-oriented perspective view of the aspiration assembly of FIG. 4A.

Adapter 202 further defines a vent 242 axially located between the first and second ledges 220, 222. Vent 242 is in fluid communication with ambient air and venting channel 240. As shown in FIGS. 4C and 4D, this allows ambient air drawn into vent 242 to flow through venting channel 240 and into the medullary canal adjacent the distal end of the aspiration assembly, while bone and/or cellular material is concurrently aspirated through the inner tube 206 in the opposite direction (e.g., from the distal end of the aspiration assembly toward the main body). The ventilated air provides airflow through the medullary canal during the harvesting process and prevents the medullary canal from becoming negatively pressurized during aspiration and, as a result, reduces the amount of blood loss that occurs during bone and/or cellular aspiration as is further explained hereinafter.

In some embodiments, the distal end 234 of inner tube 206 may be proximal to the distal end 226 of outer tube 204. The vented air is thus drawn around the distal end 234 of inner tube 206 and into the aspiration channel of the inner tube. This reduces clogging at the distal end of the aspiration assembly and maintains optimal suction or aspiration power. Moreover, because inner tube 206 is surrounded by the outer tube 204, the inner is protected from being damaged.

Figure 5A:
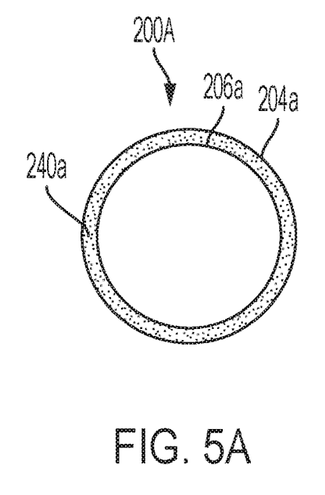
FIGS. 5A-5F are front plan views illustrating exemplary arrangements of the aspiration assembly.

Referring to FIGS. 5A-5F, various exemplary configurations of the aspiration assembly are described. FIG. 5A illustrates a preferred aspiration assembly 200A, in which inner tube 206a is coaxially positioned within outer tube 204a. Venting channel 240a is thus formed around the entire exterior surface of inner tube 206a.

Figure 5B:
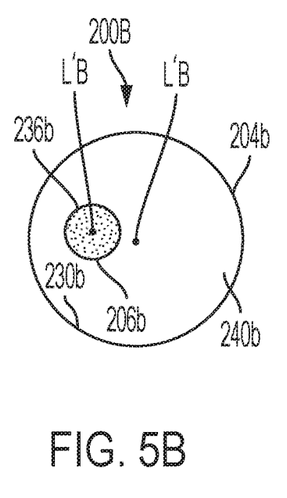

FIG. 5B shows aspiration assembly 200b, in which the longitudinal axis $L'_B$ of inner tube 206b is offset with respect to the longitudinal axis $L_B$ of outer tube 204b, and the exterior surface 236b of the inner tube is spaced from the interior surface 230b of the outer tube. Venting channel 240b entirely surrounds inner tube 206b.

Figure 5C:
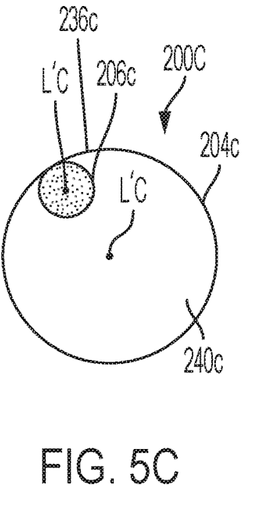

FIG. 5C illustrates a third configuration, aspiration assembly 200c, in which the longitudinal axis $L'_C$ of inner tube 206c is offset with respect to the longitudinal axis $L_C$ of outer tube 204c. In this configuration, however, a portion of the exterior surface 236c of inner tube 206c engages a portion of the interior surface 230c of outer tube 204c. Venting channel 240c is thus only formed around a portion of inner tube 206c (i.e., the portion of the exterior surface of the inner tube that is not engaged with the outer tube).

Figure 5D:
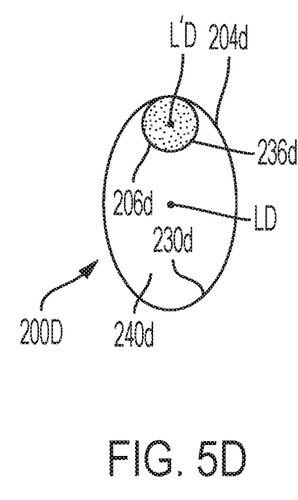

FIG. 5D illustrates aspiration assembly 200d, which is similar to aspiration assembly 200c, in that the longitudinal axis $L'_D$ of inner tube 206d is offset with respect to the longitudinal axis $L_D$ of outer tube 204d, and in that a portion of the exterior surface 236d of the inner tube is engaged with a portion of the interior surface 230d of the outer tube such that venting channel 240d is formed only around a portion of the inner tube. In this configuration, however, the cross-section of outer tube 204d is elliptical. It will be appreciated that the inner tube or the outer tube, or both the inner tube and the outer tube, of any of the configurations shown in FIGS. 5A-5F, may have a cross-section forming an ellipse, a rectangle, a hexagon or any other shape.

Figure 5E:
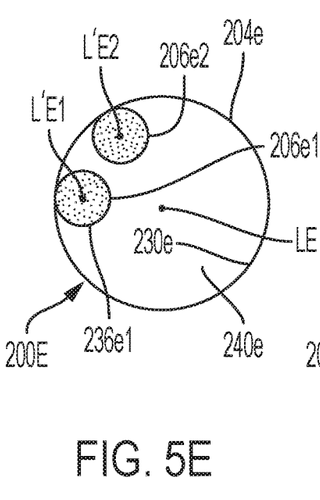

Aspiration assembly 200e, as shown in FIG. 5E, includes first and second inner tubes $206e_1$, $206e_2$. The longitudinal axis $L'_{E1}$ of first inner tube $206e_1$ and the longitudinal axis $L'_{E2}$ of second inner tube $206e_2$ are offset with respect to the longitudinal axis $L_E$ of outer tube 204e. A portion of the exterior surface $236e_1$ of first inner tube $206e_1$ and a portion of the exterior surface $236e_2$ of second inner tube $206e_2$ are engaged with portions of the interior surface 230e of outer tube 204e. Venting channel 240e is thus formed only around the portions of inner tubes $206e_1$, $206e_2$ that are not engaged with outer tube 204e. It will be understood, however, that one or both of inner tubes $206e_1$, $206e_2$ may instead be spaced from the interior surface 230e of outer tube 204e such that venting channel 240e is formed entirely around the inner tube, or the inner tubes, spaced from the interior surface of the outer tube.

Figure 5F:
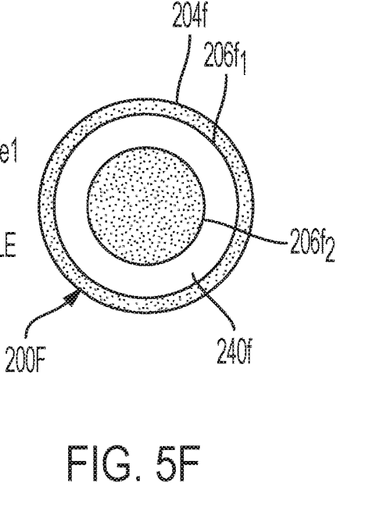

FIG. 5F illustrates aspiration assembly 200f. In this configuration, first inner tube $206f_1$ is coaxially positioned within outer tube 204f and second inner tube $206f_2$ is coaxially positioned within the first inner tube. Venting channel 240f is thus positioned between the first and second inner tubes $206f_1$, $206f_2$.

It will be appreciated that aspiration assembly 200 may be constructed as described in any one of the embodiments shown in FIGS. 5A-5F or as a combination of the same. Regardless of the specific construction, it is generally desirable that the aspiration channel (e.g., the opening of the inner tube(s)) has a cross-sectional area of at least 12 mm$^2$. Moreover, to ensure that sufficient air is vented into the medullary canal, it is desirable that the ratio of the surface area of the cross-section of the venting channel relative to the surface area of the cross-section of the aspiration channel be between 0.15 and 1.0. It will be understood that FIGS. 5A-5F illustrate the inner and outer tubes in their unbent, or not flexed, condition. Any bending or flexing of inner tube 206, relative to outer tube 204, will change the location of the aspiration channel and, in turn, venting channel 240 relative to the outer tube, but will not modify the cross-sectional area of the aspiration channel or the cross sectional area of the venting channel.

Figure 6:
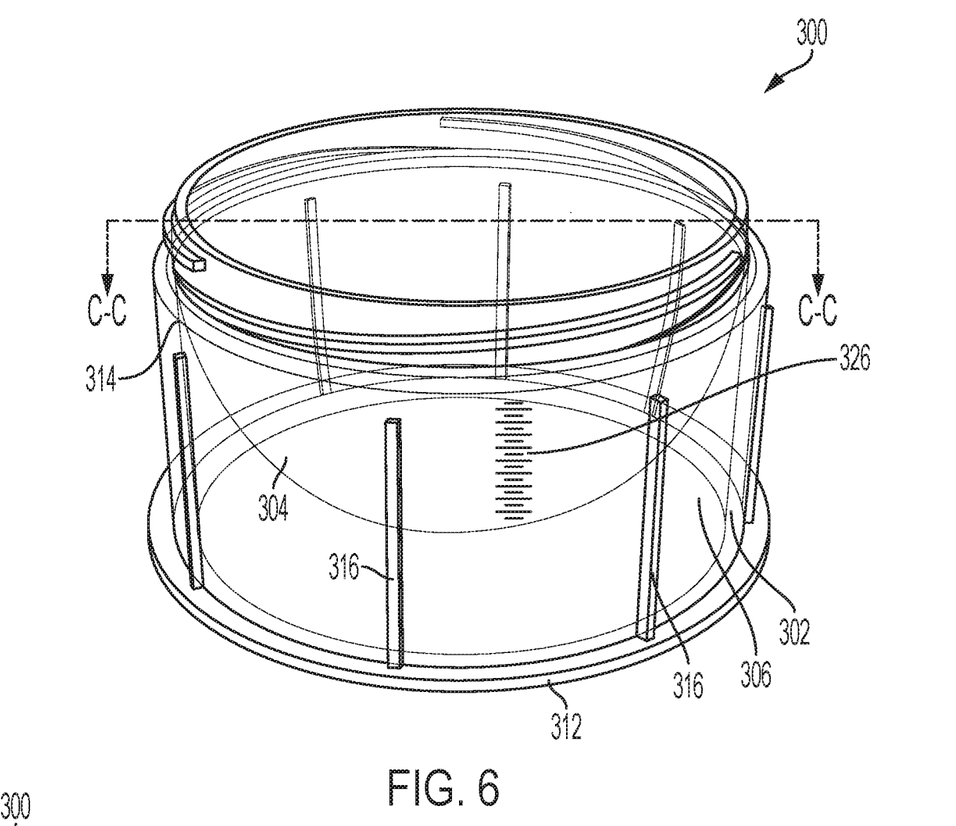
FIG. 6 is a perspective view of the collection storage container of FIG. 1.
Figure 7:
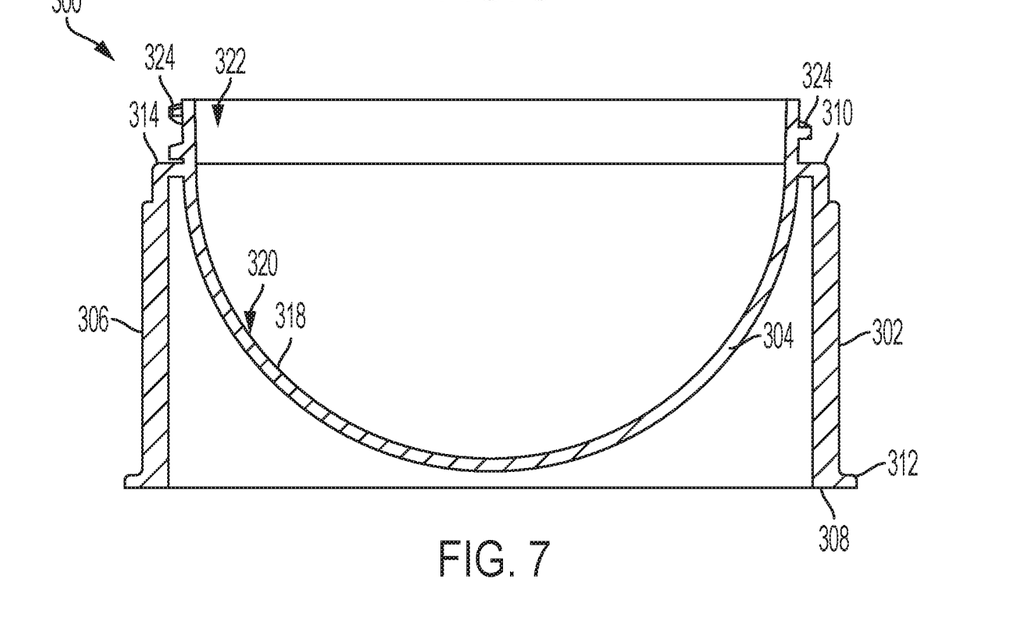
FIG. 7 is a cross-section view of the collection storage container of FIG. 6 taken along line C-C.

Turning now to FIGS. 6 and 7, storage container 300 includes a stand 302 and a collection bowl 304. Storage container 300 is preferably formed as an integral component of a plastic material, for example, through an injection molding process. Alternatively, stand 302 and collection bowl 304 may be coupled together after the components are separately manufactured.

Stand 302 may include a cylindrical sidewall 306 that extends from an annular base 308 to a top end 310 and that defines a diameter and height. Base 308 is planar and, thus, configured to rest on a flat surface, for example, an operating table. In a preferred embodiment, the diameter of stand 302 is at least 1.5 times greater than the height to save stance on soft and irregular surfaces. Base 308 may include a flange 312 for added stability.

Top end 310 preferably includes an inwardly extending lip 314 for receiving a gasket (not shown) to seal the connection between container 300 and main body 100. Sidewall 306 may include a plurality of ergonomically shaped grips 316 to aid a user in connecting the storage container 300 to the main body 100 and for removing the container from the body. Grips 316 are also thickened areas of material that strengthen sidewall 306.

Collection bowl 304 includes a sidewall 318 that is connected to lip 314 such that a first portion 320 of the collection bowl sits within the sidewall 306 of stand 302 and a second portion 322 of the collection bowl extends above the top end 310 of the stand.

As shown, the second portion 322 includes threads 324, for example, steep or bayonet threads for coupling the storage container 300 to the lid-shaped platform 104 of the main body. Collections bowl 304 may alternatively include any connector capable of removably coupling the storage container and the main body.

The inner surface of sidewall 318 is preferably smooth and hemispherical in shape. In contrast to an ordinary container having a flat base and a sidewall, the interior surface of hemispherical collection bowl 304 is devoid of edges. Because bone and/or cellular material is harvested in relatively small and finite quantities, and through an invasive surgical procedure, it is desirable to preserve all of the material that is harvested from the patient for subsequently processing. The hemispherical shape of the collection bowl 304 assists in this effort as it allows a user to easily remove all of the highly viscous bone and/or cellular material without requiring that the user attempt to scrape material from the edges or the corners of the container before inevitably leaving traces of the material behind. Thus, the hemispherical collection bowl 304 saves the user both time and hassle and maximizes the bone and/or cellular material that is eventually processed. To aid the user in removing bone and/or cellular material from collection bowl 304, the open end of sidewall 318 is preferably at least 80 mm in diameter, thereby allowing the user to easily fit his or her hand into the collection bowl and to scoop out the material, for example, using his or her fingers.

In some embodiments, an indicator scale 326 may be molded to, or imprinted on, storage container 300 such that the user can easily determine the volume of bone and/or cellular material that is present within collection bowl 304.

Bone harvesting device 10 may be used to harvest bone and/or cellular material in a harvesting method as provided herein. The method generally includes extracting bone and/or cellular material from a patient and then sending it to a storage, separation and processing facility (e.g., a "biobank") for use in a later surgical procedure involving that patient, or a different patient.

In many instances, a patient is scheduled to undergo a surgical procedure that necessitates resection of bone and/or reaming of a medullary canal of bone, but in which harvesting bone and/or cellular material is not the primary objective of the surgical procedure. For example, intramedullary nailing (IM nail) procedures, hip replacements, and knee revisions, each require a substantial amount of resection and/or reaming of bone, and therefore, generate bone and/or cellular material as a byproduct of the surgery.

During an IM nail procedure, for example, a surgeon seeking to remedy a fracture in the tibia typically first makes an incision in the patient's skin adjacent the knee. A K-wire is then introduced through the patient's skin and into an entry point on the patient's tibial plateau. In a reamed technique, the surgeon then uses the K-wire to guide a reamer through the entry point and into the medullary canal of the long bone. With the K-wire extending into the long bone and past the fracture site (e.g., so that the fracture can be properly reduced), one or more reamers are then used to bore through cortical and cancellous bone, as well as bone marrow of the patient. Because harvesting bone and/or cellular material is not the primary objective of the IM nail procedure, and extraction of these materials can often result in sever blood loss and other complication, bone and/or cellular material is generally only extracted from the medullary canal of the tibia to the extent necessary to make room for the IM implant. Any cortical bone, cancellous bone and bone marrow material that is extracted during the reaming procedure is often discarded. Using harvesting device 10, however, bone and/or cellular materials can be safely extracted from the patient for subsequent processing and reuse without placing the patient at risk.

Figure 8:
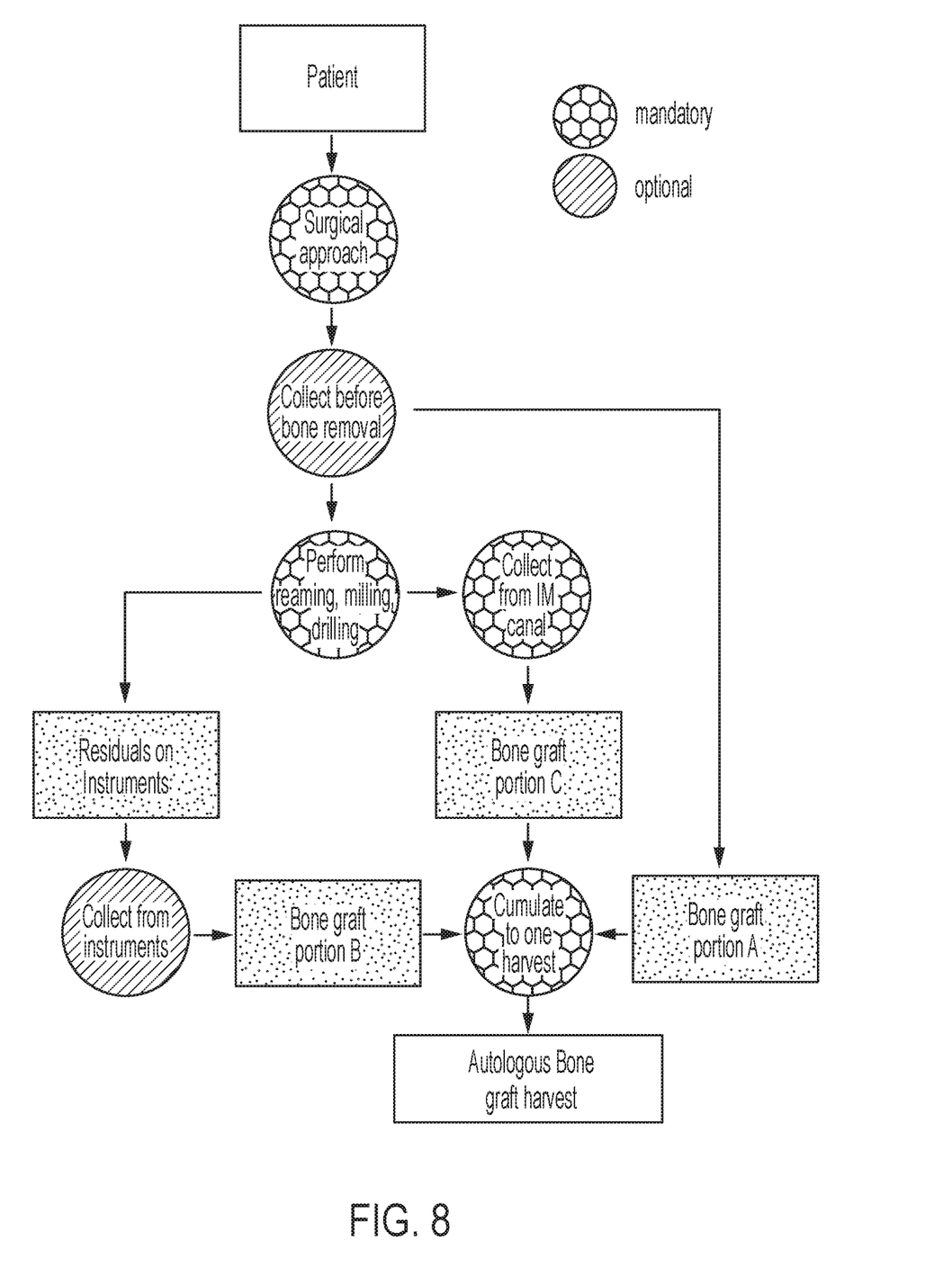
FIG. 8 is flow chart illustrating a method of harvesting bone and/or cellular material from a patient according to an embodiment of the invention.
Figure 9:
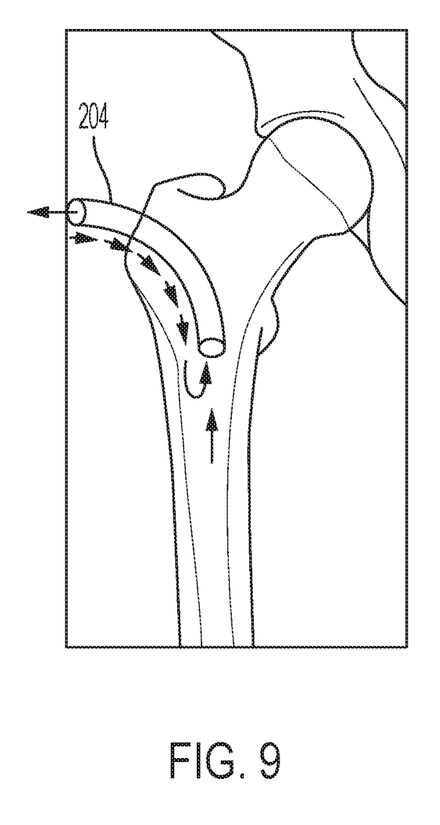
FIG. 9 is a schematic representation illustrating the bone harvesting device of FIG. 1 aspirating bone and/or cellular material from a patient's femur.

Referring to FIGS. 8 and 9, a method of extracting bone and/or cellular material from a patient is described, using an IM nail procedure remedying a patient's fractured femur as an illustrative example. It will be understood, however, that bone harvesting device 10 significantly reduces surgical complications when used to aspirate bone and/or cellular material within a medullary cavity and, thus, may likewise be used to harvest material from within the medullary canal of the tibia or any other bone from which bone and/or cellular material may be harvested.

In reducing a fractured femur, a surgeon may first approach the fracture by making an incision in the patient's skin adjacent the hip. The surgeon may then resect the greater trochanter, thereby creating an opening to the medullary canal of the femur. Resection of the greater trochanter generates loose cortical and cancellous bone, which may optionally be collected, either by hand or using bone harvesting device 10. To collect the loose cortical and cancellous bone using harvesting device 10, a user turns on the OR suction S, which generates a negative pressure in the internal cavity 112 of main body 10. Using handle 110, the user may position the distal end 210 of the aspiration assembly adjacent the resected bone, causing the loose cortical and cancellous bone to be drawn through the aspiration channel of inner tube 206, into the internal cavity, through aperture 108 in lid 104 and into storage container 300. After the loose cortical and cancellous bone has been collected, the user may turn off the OR suction S.

A K-wire may then be introduced through the patient's skin and into the medullary canal of the femur. The surgeon may then use the K-wire to guide one or more reaming, milling or drilling tools through an entry point and into the medullary canal of the femur. With the K-wire extending within the medullary canal and past the fracture site, the tool is used to bore through cortical and cancellous bone, as well as bone marrow of the patient, generating bone and/or cellular material in the medullary canal. After the surgeon is satisfied that a bore of sufficient size has been created to receive the IM implant, the tool may be removed from the patient. The surgeon may then optionally collect the residual bone and/or cellular material that adhered to the tool(s) during the reaming, milling or drilling of the medullary canal.

Before implanting the IM nail, the surgeon may utilize harvesting device 10 to safely collect bone and/or cellular material from the medullary canal of the femur. In doing so, the OR suction S is again activated. With a negative pressure generated in the internal cavity 112 of main body 110, the surgeon may position the distal end 210 of the aspiration assembly into the medullary canal of the femur such that the main body is positioned outside the patient.

Referring to FIG. 9, schematically illustrating only inner tube 206 for clarity, ambient air enters vent 242 (FIG. 4B) and flows through venting channel 240 (FIG. 4c) and into the medullary canal. At the same time, the negative pressure generated within the internal cavity 112 of main body 100 draws bone and/or cellular material through the aspiration channel of inner tube 206 and into storage container 300. Because air is continually vented within the medullary canal adjacent the distal end 210 of aspiration assembly 200, the medullary canal does not become negatively pressurized during aspiration of the bone and/or cellular material. Moreover, in the embodiment in which the distal end 234 of inner tube 206 is provided proximal to the distal end 226 of outer tube 204, the vented air is drawn around the distal end of the inner tube and into the aspiration channel thereof. The curling of the air adjacent the distal end 210 of aspiration assembly 200 guides bone and/or cellular material into the aspiration channel of inner tube 206 such that clogging is reduced and optimal suction or aspiration power is maintained.

Figure 10:
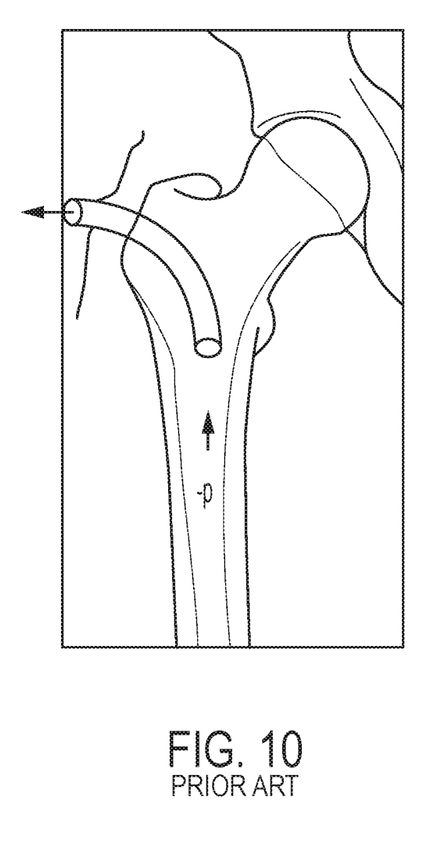
FIG. 10 is a schematic representation illustrating a known bone harvesting device aspirating bone and/or cellular material from a patient's femur.

In contrast, as is shown in FIG. 10, illustrating a known bone harvesting device that does not include the described venting features, as bone and/or cellular material is aspirated though the aspiration assembly, the medullary canal becomes negatively pressurized. The negative pressure results in the aspiration of blood and can result in sever blood loss. Additionally, as the medullary canal drops in pressure, the aspiration power of the assembly is reduced, resulting in decreased aspiration efficiency and often clogging of the assembly.

Referring back to FIG. 8, the user may optionally combine the bone and/or cellular materials into a cumulate harvest. In order to do so, the user first uncouples storage container 300 from main body 100, sticks his or her hand into collection bowl 304 and scoops out all of the bone and/or cellular material. The bone and/or cellular material may then be combined with the residual bone and/or cellular material collected from the reaming, milling or drilling tools and/or the loose bone and/or cellular material generated during the bone resection step.

After the bone and/or cellular material has been harvested, the surgeon may implant the IM nail and finish the IM nail procedure.

The bone and/or cellular material may then be sent to a biobank as separate collections, or as a cumulate harvest, for subsequent processing and use in a later surgical procedure involving that patient, or a different patient.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A bone harvesting device for extraction of bone and/or cellular material from a patient during a surgical procedure, the device comprising:
 a main body defining an internal cavity, the main body including a suction port adapted to be coupled to a suction source; and
 an aspiration assembly, comprising:
  a hollow adapter housing including a first inwardly projecting ledge, a second inwardly projecting ledge distal to the first inwardly projecting ledge, and a vent axially disposed between the first and second ledges;
  an outer tube having an interior surface, an exterior surface, a proximal end and a distal end, the proximal end of the outer tube being engaged with the second inwardly projecting ledge to form a first seal; and
  an inner tube having an interior surface, an exterior surface forming a second seal with the first inwardly projecting ledge, a proximal end and a distal end, the inner tube being in fluid communication with the internal cavity and at least partially disposed within the outer tube such that a venting channel in communication with the vent is defined between at least a portion of the inner tube and at least a portion of the outer tube,
 wherein during the surgical procedure, ambient air flows through the vent and then through the venting channel in a proximal-distal direction.

2. The device of claim 1, further comprising a storage container coupleable to the body and in fluid communication with the internal cavity for receiving bone and/or cellular material extracted from the patient.

3. The device of claim 1, further comprising the suction source in fluid communication with the body and adapted to generate negative pressure within the internal cavity of the body.

4. The device of claim 1, wherein the distal end of the inner tube is proximal to the distal end of the outer tube.

5. The device of claim 1, wherein the venting channel extends from the second seal to the distal end of the inner tube.

6. The device of claim 1, wherein the inner tube is coaxially positioned within the outer tube such that the venting channel radially surrounds the entire exterior surface of the inner tube from the second seal to the distal end of the inner tube.

7. The device of 1, wherein the hollow adapter housing is removably connectable to the main body.

* * * * *